(12) United States Patent
Bhat et al.

(10) Patent No.: US 8,865,237 B2
(45) Date of Patent: Oct. 21, 2014

(54) METHOD OF PREPARING DIALYSED EXTRACT OF FENUGREEK SEEDS WHICH INDUCES HYPOGLYCEMIA, MEDIATED, IN PART, VIA STIMULATION OF INSULIN SIGNALING PATHWAY

(75) Inventors: Manoj Kumar Bhat, Pune (IN); Maleppillil Vavachen Vijayakumar, Pune (IN)

(73) Assignees: Department of Biotechnology, New Delhi (IN); National Centre For Cell Science, Pune (ID)

( * ) Notice: Subject to any disclaimer, the term of this patent is extended or adjusted under 35 U.S.C. 154(b) by 1308 days.

(21) Appl. No.: 11/886,267

(22) PCT Filed: Jun. 27, 2006

(86) PCT No.: PCT/IN2006/000217
§ 371 (c)(1),
(2), (4) Date: Sep. 13, 2007

(87) PCT Pub. No.: WO2007/138609
PCT Pub. Date: Dec. 6, 2007

(65) Prior Publication Data
US 2009/0226554 A1    Sep. 10, 2009

(30) Foreign Application Priority Data
Jun. 1, 2006   (IN) ............................. 1326/DEL/06

(51) Int. Cl.
*A61K 36/00* (2006.01)
*A61K 36/48* (2006.01)
(52) U.S. Cl.
CPC .................................... *A61K 36/48* (2013.01)
USPC .......................................................... 424/776

(58) Field of Classification Search
None
See application file for complete search history.

(56) References Cited

U.S. PATENT DOCUMENTS

| 2005/0008716 A1 | 1/2005 | Bhaskaran et al. |
| 2005/0153001 A1 | 7/2005 | Aburdeineh et al. |

OTHER PUBLICATIONS

Vijayakumar et al. "The hypoglycaemic activity of fenugreek seed extract is mediated through the stimulation of an insulin signaling pathway". British Journal of Pharmacology vol. 146 (2005) 41-48.*
Dirk et al. "Galactomannan, soluble sugar and starch mobilization following germination of *Trigonella foenum-graecum* seeds". Plant Physiol. Biochem. vol. 37, No. 1 (1999) 41-50.*
M. V. Vijayakumar, S. Singh, R. R. Chhipa, M. K. Bhat, The hypoglycaemic activity of fenugreek seed extract is mediated through the stimulation of an insulin signalling pathway, British Journal of Pharmacology, 2005, pp. 41-48, vol. 146, Nature Publishing Group.

* cited by examiner

*Primary Examiner* — Amy L Clark
(74) *Attorney, Agent, or Firm* — The Webb Law Firm (57) ABSTRACT

A method of preparing dialysed aqueous extract of fenugreek seeds comprising washing the fenugreek seeds is distilled water, sterilizing the said seeds, subjecting the sterilized seeds to the step of grinding to form powder, suspending the said powder in phosphate buffered saline (PBS), subjecting the said suspension to the step of filtration to obtain the filtrate, treating the filtrate with activated charcoal to obtain clear supernatant, subjecting the supernatant to the step of lyophilization and the powder thus obtained was dissolved in phosphate buffered saline (PBS), dialyzing the aqueous extract of fenugreek seeds to obtain dialysed fenugreek seed extract (FSE) which was aliquoted and stored.

12 Claims, 11 Drawing Sheets

METHOD OF PREPARING DIALYSED EXTRACT OF FENUGREEK SEEDS WHICH INDUCES HYPOGLYCEMIA, MEDIATED, IN PART, VIA STIMULATION OF INSULIN SIGNALING PATHWAY

FIELD OF THE INVENTION

This invention relates to a method of preparing dialysed aqueous extract of fenugreek seeds which induces hypoglycemia, mediated, in part, via stimulation of insulin signaling pathway.

BACKGROUND OF INVENTION

Diabetes mellitus is an alarming medical problem affecting more than 194 million people. Persisting diabetic conditions often lead to damage of blood vessels, increased risk of coronary artery disease, myocardial infarction, atherosclerosis, claudication and stroke, blindness, nerve damage and in extreme situations may event lead to amputations. The principal cause of these complications is hyperglycemia mainly due to lack of insulin, or insulin resistance, or defects in insulin signaling pathways.

Management of diabetes focuses mainly on several approaches intended to sustain reduction in hyperglycemia that reduces the risk of developing microvascular and macrovascular complications. In addition to insulin, control of hyperglycemia mainly involves use of biguanides, sulfonylureas, D-phenylalanine derivatives, meglitinides, peroxisome proliferator-activated receptor-γ (PPAR-γ) agonists (thiazolidine diones) and α-glucosidase inhibitors. These drugs augment insulin secretion from pancreatic islets, act to reduce hepatic glucose production, interfere with gut glucose absorption or enhance insulin action, suppress glucose production and augments glucose utilization. The efficacies of these compounds are still under debate due to either side effects or many patients who respond initially become refractory to treatment over a period of time. Considering the multifactorial nature of diabetes that can not be ascribed to a single genetic or environmental change but arise from a combination of genetic, environmental or behavioral factors, alternative approaches are necessary for better management. Extracts of seeds and leaves of fenugreek have been historically known for their antihyperglycemic activity and non-toxicity. Though hypoglycemic effects of fenugreek have been attributed to several factors and mechanisms, its active principles have been only partially purified viz., trigonelline and 4-hydroxyisoleucine, which account for the antidiabetic activity in part. They are shown to be act by enhancing insulin secretion from islets of Langerhans. So far no attempts have been made to explore the possibility of insulin mimicking effect of fenugreek seeds extract at cellular and molecular level.

Fenugreek and other traditional plants are currently being investigated for their potential as a source of new hypoglycaemic compounds for the treatment of diabetes. However, with the exception of guanidine, many of the hypoglycaemic compounds isolated from plants are small molecules such as alkaloids, flavanoids, glycosides, steroids, aminoacids or minerals that are not suitable for pharmaceutical drug development. However, medicinal plant extracts used for treating hyperglycemia might contain number of components that together contribute to over-all effectiveness. Therefore isolating individual component from such extracts may not be as effective.

OBJECTS OF THE INVENTION

An object of this invention is to propose a method of preparing dialysed aqueous extract of fenugreek seeds.

An object of this invention is to prepare a dialysed aqueous extract of fenugreek seeds which stimulates glucose dependent pancreatic insulin secretion.

Still another object of this invention is to propose a dialysed aqueous extract of fenugreek seeds which activates insulin signaling pathway in adipocytes and liver that enhance glucose uptake.

Further object of this invention is to prepare a dialysed aqueous extract of fenugreek seeds which enhances glucose utilization by the activation of liver glucokinase enzyme.

Still further object of this invention is to give a scientific validation for the hypoglycemic activity using innovative strategies.

Statement of the Invention:

According to this invention this is provided a method of preparing a dialysed aqueous extract of fenugreek seeds comprising washing the fenugreek seeds in distilled water, sterilizing the said seeds, subjecting the sterilized seeds to the step of grinding to fine powder, suspending the said powder in phosphate buffered saline (PBS), subjecting the said suspension to the step of filtration to obtain the filtrate, treating the filtrate with activated charcoal to obtain clear supernatant, subjecting the supernatant to the step of lyophilization and the powder thus obtained was dissolved in phosphate buffered saline (PBS), dialyzing the aqueous extract of fenugreek seeds to obtain dialysed fenugreek seed extract (FSE) which was aliquoted and stored.

This invention highlights the fact that the said dialysed fenugreek seed extract (FSE) does possess in vivo hypoglycemic activity.

The hypoglycemic effect was associated with significant enhancement in liver glucokinase activity.

Hypoglycemic effect was sustained for further five days following consecutive administration of said extract for five days.

Dialysed aqueous extract of fenugreek seeds potentiated the glucose-dependent insulin secretion in normal mouse islets and increased GLUT4 translocation dependent glucose uptake in cells.

Similar to insulin, the said extract induced tyrosine phosphorylation of a number of proteins including insulin receptor, IRS-1 and p85 subunit of PI3-Kinase, in both 3T3-L1 adipocytes and hepatoma cell line, HepG2.

Therefore the hypoglycemic activity of dialysed aqueous extract of fenugreek seeds is a cumulative effect of three independent actions; 1) it stimulates glucose dependent pancreatic insulin secretion, 2) metabolic effects in adipocytes and liver that enhances glucose uptake mediated via activation of insulin signaling pathway and, 3) enhances glucose utilization by activation of liver GK enzyme. Also, the in vitro models and methods described in this study could be used for screening the activity of natural compounds suitable for the development of new antidiabetic drugs.

DETAILED DESCRIPTION OF THE INVENTION

Preparation of Fenugreek Seeds Extract. Fenugreek Seeds were Washed in distilled water, surface sterilized by soaking for 30 seconds in 0.1% sodium hypochlorite and 0.05% nonidet P-40 and rinsing thoroughly with distilled water. Seeds were ground to fine powder in mixer at chilled conditions, and Suspended in PBS (pH 7.4) containing 1 mol/l PMSF and protease inhibitor cocktail. The extract was filtered through three-layered cheesecloth. Filtrate was treated with activated charcoal, kept on ice for 1 h and centrifuged at 15,000×g at 4° C. for 30 min and clear supernatant was lyophilized. The powder was dissolved in PBS and dialyzed in 8000 Dalton cut off dialysis membrane for 24 h with 6 hourly changing of PBS. This preparation is referred as FSE. The FSE was aliquoted and stored at −70° C. for long term and this was used for all further experiments.

In vivo antihyperglycemic activity of dialyzed FSE in chemically induced diabetic animal models. BALB/cJ or Swiss albino mice (male, 8-10 week old) were housed under environmentally controlled conditions (22+/−2° C.) with a 12 h light/dark cycle and had free access to standard rodent pellet food and water. Animals were given 5 daily intraperitoneal (IP) injection of freshly prepared STZ (40 mg/kg in 0.5 mol/l sodium citrate pH 4.5) or AXN (50 mg/kg in 0.9% sodium chloride). Ten hours before the experiments, animals were moved to new cages in which no food was available. AXN injected mice that achieved a glucose level of 200-300 mg/dl and STZ injected mice that achieved a glucose level of 275-400 mg/dl were used as hyperglycemic models in this study. Mice were divided into, diabetic control group, insulin group and FSE group (n=5 in each group). Mice were injected (IP) with vehicle (PBS), insulin (1.5 U/kg) or extract (1, 5 or 15 mg/kg). Blood was collected before injection (0 min), 90 and 240 min after the treatments and serum blood glucose levels were estimated. In some experiments STZ-BALB/cJ mice were sacrificed 90 min after the treatments, and the livers were harvested for analysis. In another set of experiments, AXN-induced Swiss albino diabetic mice were injected with PBS or extract for 5 days (n=5). Blood was collected on day 0, 5, 10 and 15 and body weight was monitored on same day. Acidified insulin from bovine pancreas diluted in PBS was used as a positive test compound in all the experiments. All animal experiments have been performed following the requirement of the committee for the Purpose of Control and Supervision of Experiments on Animals (CPCSEA), Government of India, and after permission of the Institute's Animal Care and Use Committee (IACUC).

Effect of FSE on intraperitoneal glucose tolerance test (IPGTT) in normal animals. The IPGTT was performed by IP injection of 3 g/kg of glucose after 10 h fasting to induce hyperglycemia (n=5). Blood collected before the injection of glucose was considered as basal. Fifteen mg/kg FSE was injected 10 min after the injection of glucose. Same dose of FSE was injected to normoglycemic (glucose unloaded) mice. Blood samples were collected at 45, 90 and 180 min after the administration of extract and blood glucose levels were estimated.

Glucokinase assay. Liver samples were homogenized in three volumes of ice cold buffer containing 50 mmol/l Tris-HCl, pH 7.4, 300 mmol/l sucrose, 100 mmol/l KCl, 1 mmol/l EDTA 2.5 mmol/l mercaptoethanol and centrifuged at 12,000×g for 15 min (12). The resulting supernatants were centrifuged at 180,000×g for 60 min. This cytosolic fraction was used to assay GK activity, by a spectrophotometric assay essentially as described previously (23). GK activity was calculated as the difference between the glucose phosphorylation capacity at 100 and 0.5 mmol/l glucose. Enzyme activity is indicated as $nmol.min^{-1}.mg^{-1}$ of protein.

Effect of FSE on insulin secretion in islets. Group of five Swiss albino mice weighing 18-20 g were sacrificed, pancreata were removed aseptically, and islets were prepared as described previously (24) by digestion of pancreas with a collagenase solution (BSA 2%, trypsin inhibitor Type II 0.2%, collagenase Type IV 0.1%, in DMEM) for 20 min. Islets were maintained in RPMI supplemented with 10% FBS, 100 U/ml penicillin 100 µg/ml streptomycin at 37° C. in 5% $CO_2$ After 48 h, islets were washed thrice with Krebs Ringer buffer (KRB) (120 mmol/l NaCl, 5 mmol/l KCl, 2.5 mmol/l $CaCl_2$, 1.1 mmol/l $MgCl_2$, 25 mmol/l NaHCO3. pH7.4) by centrifugation at 1000×g. Islet viability was assessed by trypan blue staining and specificity of islets was determined by dithiozone (0.01%) staining for 10 min at 37° C. Hundred islets were preincubated in KRB containing 0.1% BSA and 3.3 mmol/l glucose for 1 h at 37° C. in 5% $CO_2$. Subsequently islets were incubated for additional 1 h with or without FSE in presence of 16.7 mmol/l glucose. Culture supernatants were collected and assayed for the insulin by using ultrasensitive mouse insulin ELISA kit (Mercodia, Uppsala, Sweden)

Cell Culture In Vitro Studies. 3T3-L1 preadipocytes (ATCC no. CL-173) and HepG2 cells (ATCC no. HB-8065)

were maintained in 100 mm coated petri plates in DMEM containing 25 mmol/l glucose and 10% NBCS or PBS respectively. For preadipocyte differentiation 80% confluent preadipocytes were cultured for 2 days in differentiation medium (DMEM supplemented with 1 μmol/l insulin, 0.5 mmol/l IBMX, 0.25 μmol/l DEX containing 10% FBS) and for 2 days in DMEM supplemented with 1 μmol/l insulin and 10% FBS. Thereafter the cells were grown for an additional 4-5 days in DMEM containing 10% FBS. Media was changed on every second day without any additional supplements. CHO clones expressing insulin receptor and GLUT4eGFP protein were grown in media supplemented with hygromycin additionally (100 μg/ml). Penicillin (100 units/ml) and streptomycin (100 mg/ml) were added routinely to cultures and all cell lines were cultivated at 37° C. in a 5% $CO_2$ enriched humidified atmosphere.

Effect of FSE on glucose transport. CHO clones expressing insulin receptor and GLUT4eGFP were grown in 24 well plates, serum starved for 3 h in DMEM containing 0.1% BSA and washed twice in KRB buffer (137 mmol/l NaCl, 4.7 mmol/l KCl, 10 mmol/l sodium phosphate pH 7.4, 0.5 mmol/l $MgCl_2$, 1 mol/l $CaCl_2$, 2 mg/ml BSA) at 37° C. for 30 min (25). Cells were then treated with insulin or FSE for an additional 10 and 30 min respectively. The glucose uptake reaction was initiated by adding 0.1 mmol/l 2-deoxy glucose containing 0.5 μCi/ml 2-DG. After incubation at 37° C. for 4 min, the reaction was terminated by washing tree times with ice-cold PBS buffer containing 20 mmol/l D-glucose, and solubilized with 0.1% SDS. Protein was estimated and the radioactivity incorporated into cells was quantified by scintillation counting (Packard, Albertville, Minn.). Nonspecific uptake, measured in the presence of 10 μmol/l cytochalasin B, was subtracted from all values. To examine the specificity of the signaling pathway cells were pre-treated with 100 mmol/l wortmannin, a P13-K inhibitor, for 20 min or 100 nmol/l BIS-1, a PKC specific inhibitor for 1 h and followed by treatment with extract additional 30 min.

GLUT4 Translocation Assay in GLUT4 Overexpressing Cell lines. CHO clones expressing insulin receptor and GLUT4eGFP protein were plated on a microscopic chamber slide (ICN, Costa Mesa, Calif.), serum starved in DMEM containing 1 mg/ml BSA for 3 h, followed by treatment with 100 nmol/l insulin or 25 mg/l FSE for 10 and 30 min respectively. Treatment was terminated by keeping the slide on ice and washing with cold PBS. Cells were fixed with 3% paraformaldehyde (PF) in PBS for 15 min at room temperature. GLUT4 translocation was investigated by using LSM confocal microscope (Zeiss LSM 510, Heidelberg, Germany). 3T3-L1 expressing mycGLUT4 were grown in 96 well plated then differentiated to adipocytes, serum starved for 3 h and incubated with insulin or FSE for 10 and 30 min respectively. To examine the specificity of the signaling pathway the cells were pretreated with wortmannin (100 nmol/l) or BIS-1 (100 nmol/l) for 20 min and 1 h respectively. The reaction was terminated by keeping the plate on ice and washing with cold PBS followed by fixing the cells with 3% PF for 3 min and then neutralized with 1% glycine in PBS at 4° C. for 10 min (26, 27). After blocking the cells with 5% skimmed milk in PBS at room temperature for 30 min, cells were incubated with 1:200 dilution of monoclonal anti-myc antibody at 4° C. for overnight. Cells were washed with PBS-T (PBS containing 0.05% Tween 20) and subsequently incubated with peroxidase conjugated goat anti-mouse IgG (1:1000, 4° C.) for 1 h. Following the removal of secondary antibody, cells were incubated with 5% ABTS containing 1% $H_2O_2$ in citrate buffer pH 4.2. The optical absorbance of the supernatant was measured at 414 nm.

Effect of FSE on insulin signaling proteins in 3T3-L1 Adipocytes and HepG2 cell lines. Differentiated 3T3-L1 adipocytes or HepG2 cell were serum starved in F-12K medium containing 7 mM glucose and 0.1% BSA for 16 h followed by changing medium to DMEM containing 25 mmol/l glucose and incubated for 1 h. Subsequently the cells were treated with 100 nmol/l insulin or 25 mg/l FSE for 10 min and 30 min respectively. Untreated cells were incubated with PBS. Cells were washed with cold PBS, removed from the plates using a rubber policeman, lysed in lysis buffer (50 mmol/l Tris-HCl pH7.5, 150 mmol/l NaCl, 1% NP-40, 2 mmol/l EGTA, 2 mmol/l $Na_3VO_4$, 100 mmol/l $Na_4P_2O_7$, 50 mmol/l okadaic acid, 1 mmol/l PMSF and protease inhibitor cocktail) on ice for 30 min, passed through 261/2G syringe 20 times and finally centrifuged at 15,000×g for 10 min at 4° C. Equal amounts of protein (100 μg) were diluted in 5× Laemmli reducing buffer (250 mmol/l Tris-HCl p 6.8, 10% SDS, 0.5% bromophenol blue, 50% glycerol, 12.5% β-mercaptoethanol) boiled for 5 min at 100° C. and resolved by 8% SDS-PAGE by running proteins below 43 kDa out of the gel. The proteins form the gel were transferred to nitrocellulose membrane using transfer buffer (CAPS buffer pH 10.7 containing 10% methanol) by applying 150 mA current for 2 h. Thereafter membranes were washed and blocked with 5% BSA or non fat skimmed milk in tris-buffered saline (TBS) (10 mmol/l Tris-HCl pH7.5, 1.5 mol/l NaCl) for overnight at 4° C., washed with TBS-T (TBS containing 0.1% Tween-2-), incubated with anti-phosphotyrosine antibody or anti-phospho-Akt (Ser-473)-R or (Thr308)-R antibody for 2 h at room temperature, washed extensively, incubated with peroxidase conjugated secondary antibody and processed for enhanced chemiluminescence. For reprobing, membranes were washed (62.5 mmol/l Tris-HCl (pH 6.7), 2% w/v SDS and 100 mmol/l β mercaptoethanol) for 30 min at 50° C., and incubated with either anti-IR-α or anti-IRβ or anti-IRS-1, or anti-p85 or anti-Akt antibody.

Confocal microscopy analysis of PKC translocation in HepG2 cells. HepG2 cells were serum starved for 3 h and were treated with either 100 nmol/l insulin for 10 min or 25 mg/l FSE for 30 min. In some wells, cells were pretreated with pharmacological inhibitors before treating with extract. Cells were washed quickly with cold PBS and fixed by treating with 3% paraformaldehyde in PBS Ph 7.4, for 15 min at room temperature, rinsed with PBS three times and quenched with 1% glycine for 10 min. Cells were permeabilised with 0.025% saponin in PBS, for 5 min, blocked with PBS containing 5% FBS for 1 h at room temperature, incubated with anti-PKC antibody for overnight at 4° C. in PBS oontaining 2.5% FBS. Cells were washed four times for 5 min each with PBS. Cells were then incubated with a flourescein isothoicyanate conjugated anti-rabbit antibody for additional 1 h, washed again and mounted using vectashield (Vector Laboratories, Burlingame, Calif.) for visualization by confocal microscopy. Rabbit IgG was used as an isotype control.

Isolation of plasma membrane fraction and immunoblotting detection of PKCλ and GLUT4 in 3T3-L1 adipocytes. Differentiated 3T3-L1 cells in 100 mm petri dishes were serum starved for 3 h in DMEM supplemented with 0.1% BSA and then treated with 100 nmol/l insulin or 25 mg/ml FSE for 10 min and 30 min respectively. In some cases cells were pre-treated with 100 nmol/l wortmannin, for 20 min or 100 nmol/l BIS-1 for 1 h followed by treatment with extract t for additional 30 min. Plasma membrane fractionation of 3 T3-L1 adipocytes was performed as previously described (28) with slight modifications that 1 mmol/l PMSF, 1 mmol/l $Na_3VO_4$ and a cocktail of protease inhibitors were added to the lysis buffers. Equal protein was diluted with 5× Laemmli buffer, electrophoresied by 10% SDS-PAGE and transferred on to a nitrocellulose membrane. The membrane was probed with anti-nPKCλ or anti-GLUT4 antibody.

EGFR auto phosphorylation in A431 cells. A-431 epidermal carcinoma cells (ATCC no. CRL-1555) were maintained in DMEM containing 10% FBS, serum starved followed by treatment with 50 nmol/l epidermal growth factor (EGF) (Promega, Madison, Wis.), or FSE for the indicated period of time. The cells were washed with PBS, lysed, and equal amount (50 μg) of protein were resolved by SDS-PAGE, transferred to nitrocellulose membrane, blocked, and probed with antiphosphotyrosine antibody. Same membrane was stripped and reprobed with anti-EGFR antibody.

Figure 1:
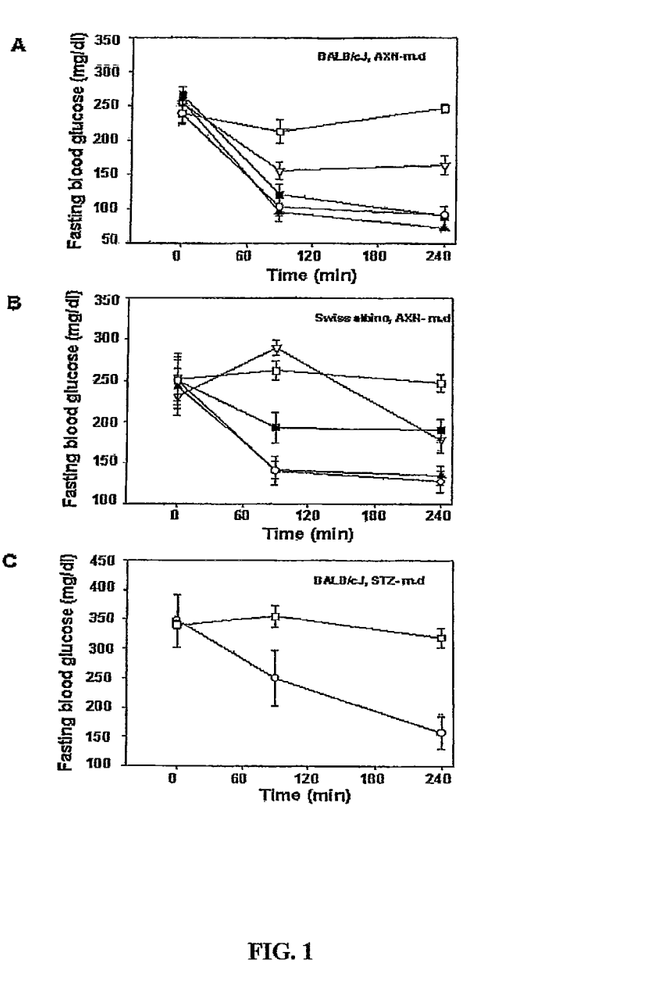
FIG. 1: The in vivo effectiveness of FSE was studied in diabetic fasted BALB/CJ or Swiss albino mice in which diabetes was induced by injecting multiple doses of STZ or AXN.
Figure 2:
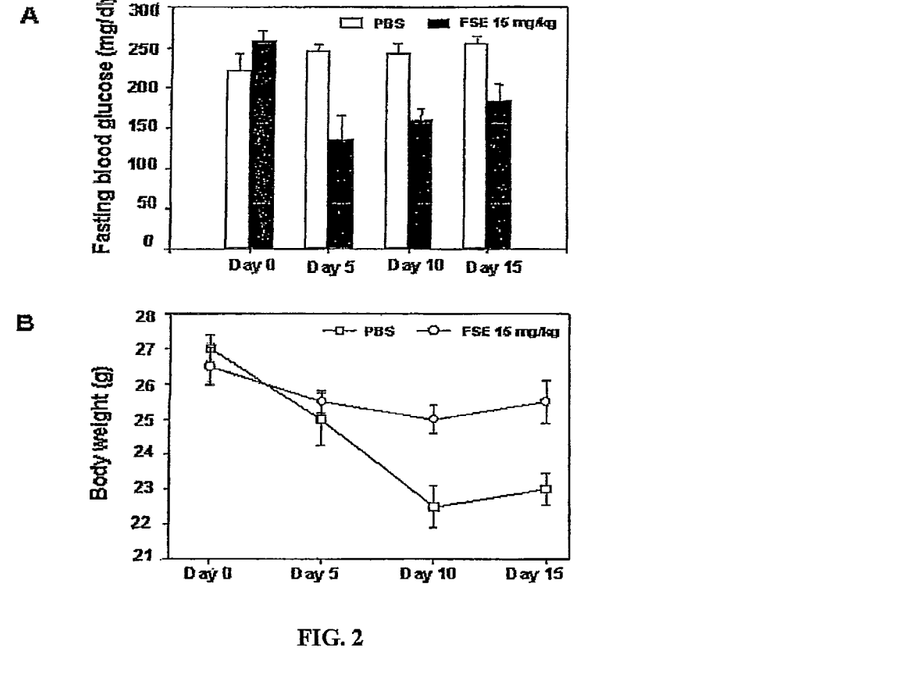
FIG. 2: Acute and chronic administration of FSE for 5 days in diabetic Swiss albino mice decreases blood serum glucose and improves bodyweight.

Antidiabetic effect of fenugreek seeds extract is currently under intense investigation. Though few factors like trigonelline and 4-hydroxyisoleucine, which exhibit hypoglycemic effect, have been reported, none of them have reached a stage for human use. Based on the literature, we felt that the whole FSE extract may function more efficiently than certain individual components. Therefore, we attempted to understand the mechanism of action of FSE, which will be of immense use for ascertaining the antidiabetic potential of FSE. Though the American Diabetes Association encourages the use of traditional medicines, the World Health Organization (WHO) expert committee on Diabetes Mellitus recommended that clinical use of traditional antidiabetic plants warrant further evaluation. So far none of the studies have simultaneously investigated effect of FSE or any other plant extract on various pathways involved in glucose metabolism and regulation. The data presented in FIG. 1, clearly demonstrates that FSE significantly improves glucose homeostasis in different diabetic mice strains obtained by injection of multiple doses of either AXN or STZ. At a dose of 15 mg/kg FSE produced a 50-60% decrease in fasting blood glucose level. In addition FSE also improved intraperitoneal glucose tolerance by effectively lowering blood glucose in normal Swiss albino mice after they were injected with glucose solution. It is pertinent to test the maintenance of lower blood glucose levels with long-term treatment rather than the acute hypoglycemic effect after a single does. The present study demonstrates that antidiabetic potential of the FSE remained effective for 10 days without significant loss in body weight after 5 consecutive FSE injections in AXN induced diabetic mice (FIG. 2).

Insulin secreted by islets of Langerhans, in response to increase blood glucose level, acts on target tissues viz adipose tissue and liver. Glucose homeostasis is lost because of combined defects in insulin secretion and insulin action leading to hyperglycemia. In our present study we report that FSE treatment in diabetic animals for 90 min results in the activation of GK by 3.5 fold compared to control treated animals. Under the similar experimental conditions insulin treatment resulted in an increase in GK activity by 4.5 fold which is marginally higher than FSE treated mice. Moreover, GK activity in FSE treated diabetic mice was even higher than that of healthy non-diabetic control mice (Table 1). These results clearly suggest that one of the mechanisms by which FSE treatment leads to glucose lowering effects is via activation of glucose metabolizing enzyme in the liver.

Figure 3:
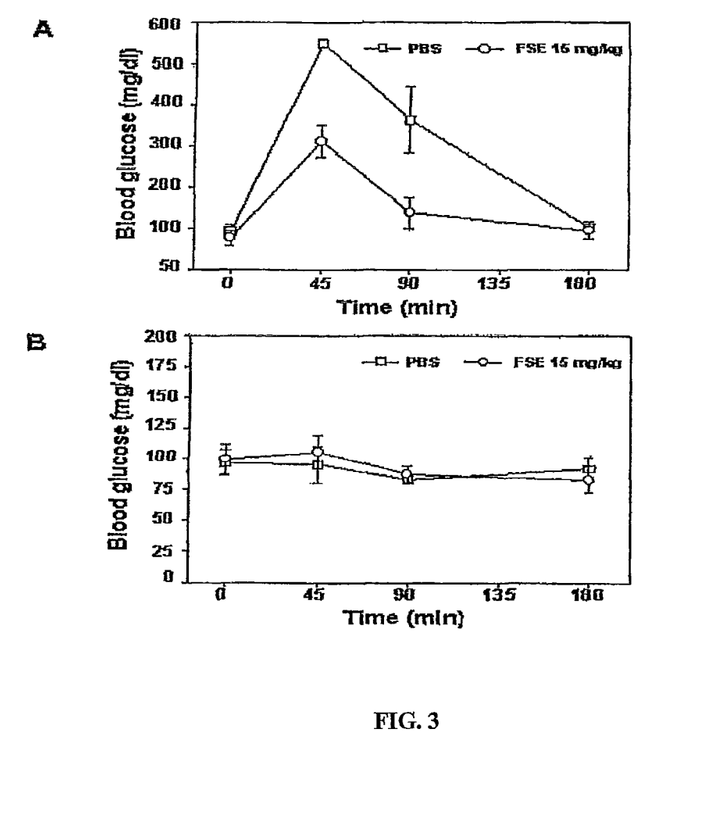
FIG. 3: Effect of FSE on intraperitoneal glucose tolerance test (IPGTT) in normal Swiss albino mice.
Figure 4:
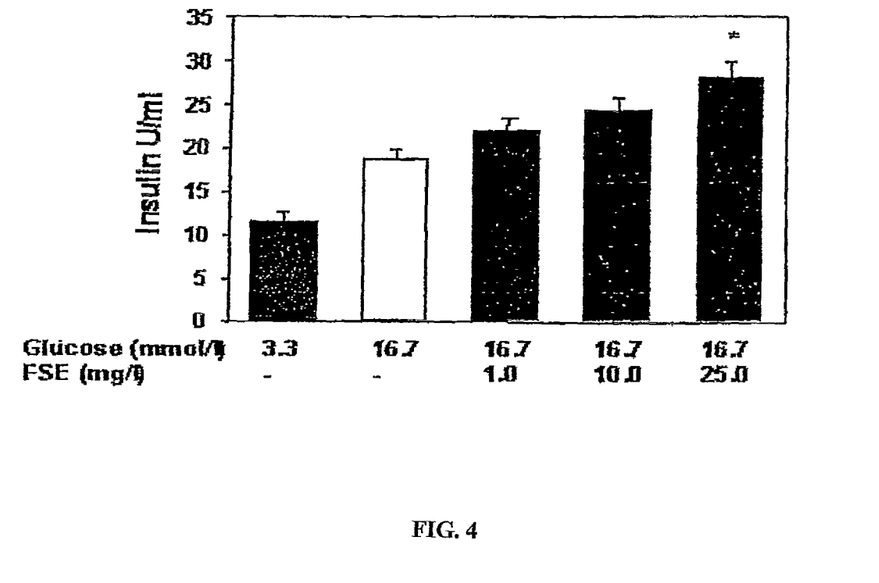
FIG. 4: Glucose stimulated insulin release from isolated islets of Langerhans is potentiated by FSE.

To explain the 50-60% reduction in blood glucose level after the administration FSE, the mechanisms by which FSE ameliorates hyperglycemia was further investigated in vitro. The effect of FSE on pancreas and target tissues of insulin viz., liver and adipocytes, were explored using in vitro models and its effects were compared with that of insulin. Firstly, effect of FSE on insulin secretion by mouse islets was investigated. As shown in FIG. 4, FSE potentiated the insulin secretion induced by glucose treatment in a dose dependent manner. At a dose of 25 mg/l FSE, insulin secretion increased by ~1.5 fold. Since normoglycemic animals were not sensitive to the glucose-lowering effects caused by extract (FIG. 3B), the mechanism of action of FSE is partly dependent on blood glucose level, which is a hallmark for diabetic condition.

Figure 6:
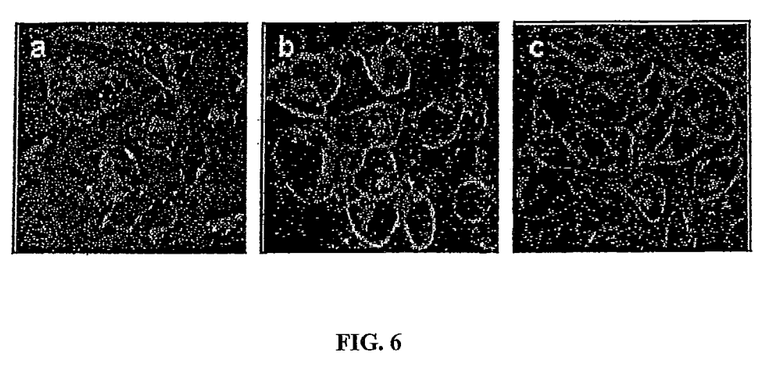
FIG. 6: Analysis of FSE induced GLUT4 translocation.
Figure 7:
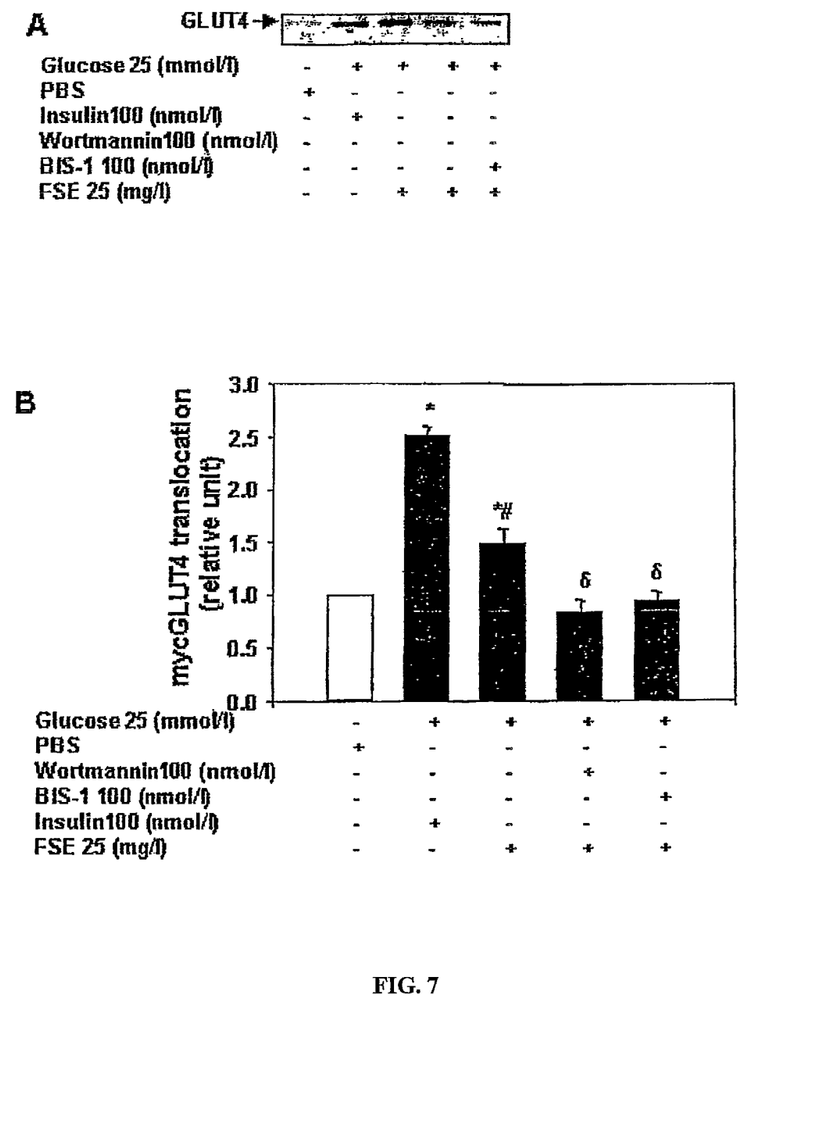
FIG. 7: Effect of FSE on GLUT4 translocation and specificity in 3T3-L1 adipocytes. Pretreatment with wortmannin and BIS-1 masked there effects.
Figure 9:
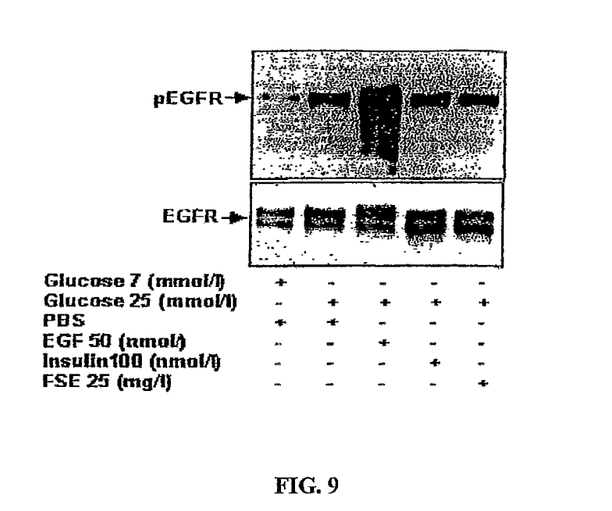
FIG. 9: FSE is not a general tyrosine kinase activator of receptors. FSE failed to activate EGF receptor as treatment did not increase the autophosphorylation of it.

Glucose uptake by target tissues of insulin is the rate-limiting step in type 2 diabetes. This transport is facilitated mostly by translocation of glucose transporter form intracellular site to the plasma membrane in the target tissues. Using stable clones overexpressing GLUT4 as an in vitro model system, we demonstrate that FSE treatment induces a rapid stimulation of cellular glucose uptake by activating cellular responses that lead to glucose transporter translocation to cell surface (FIGS. 6, 7A and B). In comparison to insulin treatment, the potency of FSE in stimulating glucose uptake was less by 35% ($P<0.05$ vs. insulin; FIG. 4B). In 3T3-L1 cells overexpressing GLUT4 treatment with FSE increased GLUT4 translocation increased by 1.4 fold in comparison to the basal levels of GLUT4. Under similar experimental conditions, 100 nmol/l insulin treatment enhanced the glucose uptake by 2.5 fold. These results suggest that the factor(s) in FSE, in addition to stimulating GK and potentiating insulin secretion. The action of insulin is initiated by binding to the insulin receptor, which leads to activation of its receptor tyrosine kinase and autophosphorylation (6). Similarly, treatment of HepG2 and 3T3-L1 cells, with 25 mg/l FSE activated the tyrosine phosphorylation of 1R-β and subsequently enhancing phosphorylation of downstream signaling molecules like IRS-1 as well as p85 subunit of P13-kinase. FSE had no effect on IR-α phosphorylation. Moreover, FSE treatment activated specifically the IR signaling pathway since, it did not enhance EGF receptor autophosphorylation (FIG. 9). Therefore, FSE can act as an insulin mimetic molecule and it is not a general sensitizer of receptor tyrosine kinase domains.

Figure 5:
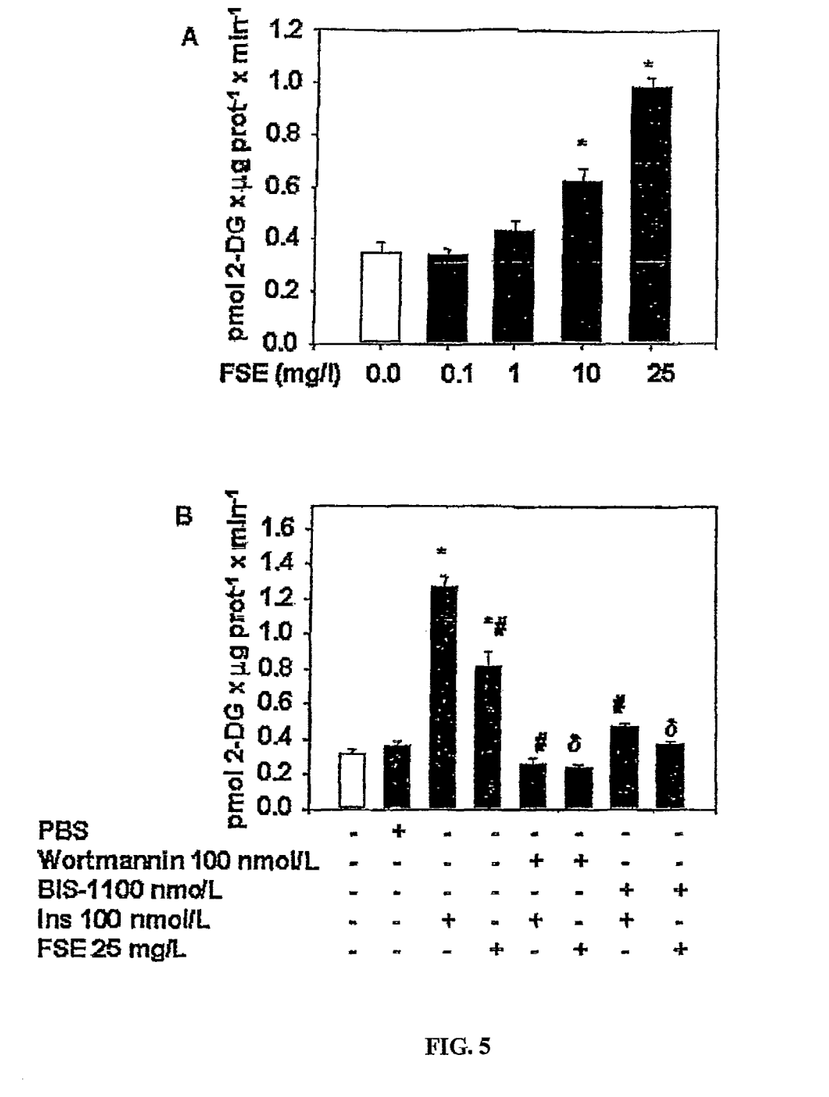
FIG. 5: Effect of FSE on glucose transport in cells. FSE treatment exhibited a dose dependent increase in glucose transport rates in this cell based model.
Figure 10:
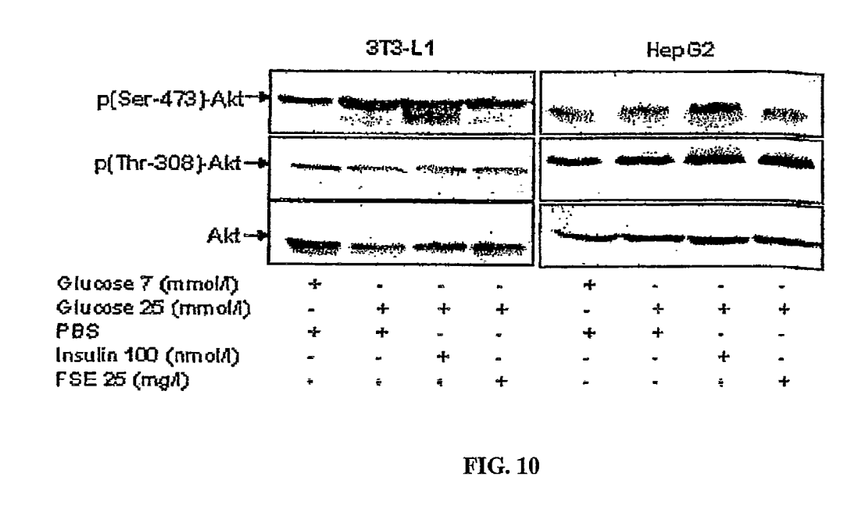
FIG. 10: Effects of FSE are independent of Akt activation. Effect of insulin and extract on activation of Act shows significant differences.
Figure 11:
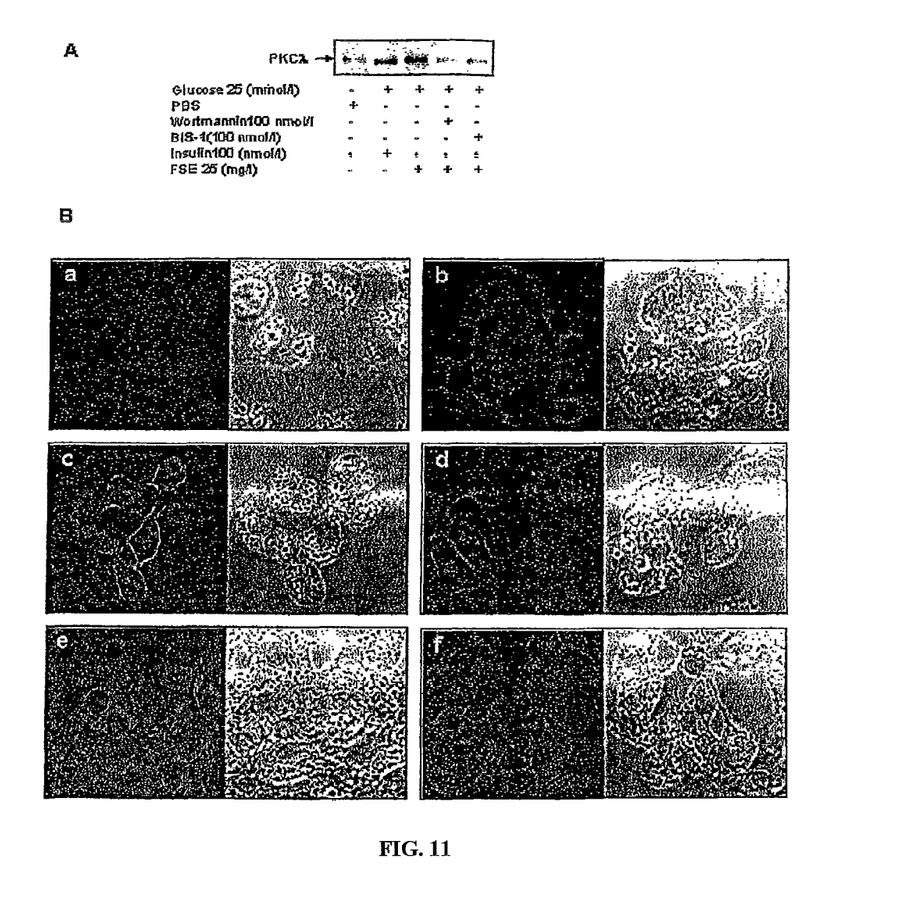
FIG. 11: To investigate the link between FSE induced IR phosphorylation and GLUT4 translocation, translocation of PKCλ was studied in both 3T3-L1 and HepG2. Significant amount was detected in membrane fraction.
Figure 12:
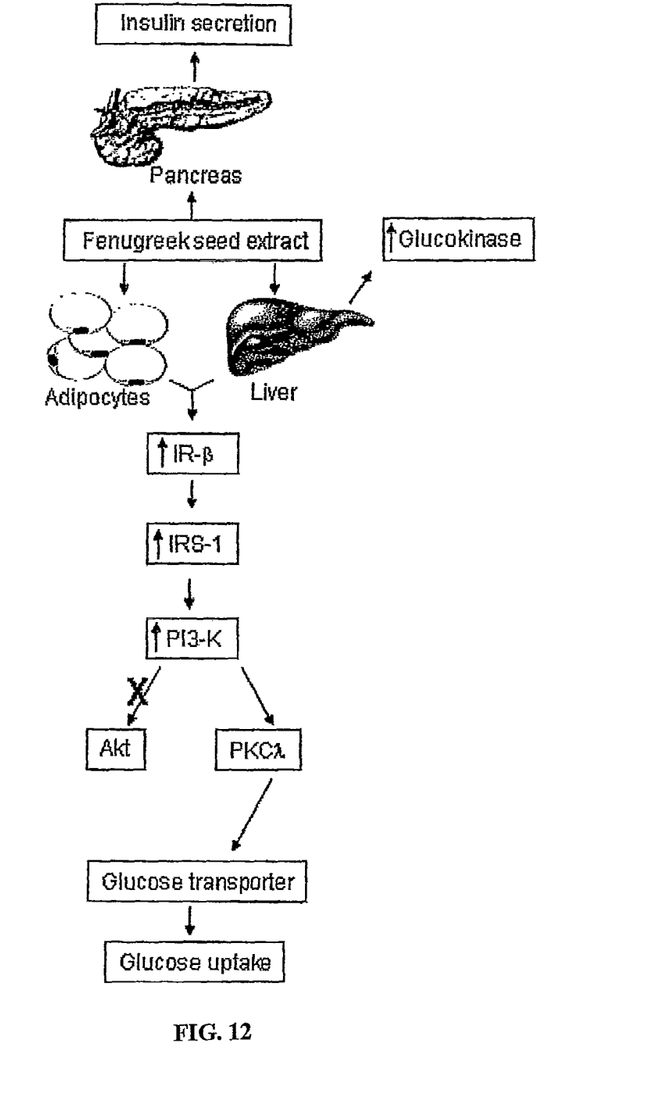
FIG. 12: A model for cellular effects of fenugreek seeds extract on glucose homeostasis.

Activation of P13-K is necessary for the metabolic action of insulin, action of insulin, as demonstrated in studies using P13-K inhibitors wortmannin. Pretreatment of cells with wortmannin inhibited GLUT4 translocation as well as glucose uptake (FIG. 5B, FIGS. 7A and B). Insulin elicited signals resulting in activation of P13-K are transmitted by two independent pathways; an Akt pathway and a PKC pathway, down stream of P13-K (9). FSE treatment had no effect on Thr-308 or Ser-473 phosphorylation of Akt in both 3T3-L1 and HepG2 cells (FIG. 10). However FSE treatment did activate translocation of PKCλ in both 3T3-L1 adipocytes and HepG2 cells (FIGS. 11A and B). To further confirm the involvement of PKCλ, pretreatment of cells with wortmannin and BIS-1, a PKC specific inhibitor inhibited translocation of PKCλ induced by FSE. Therefore, in contrast to involvement of PKCλ and Akt in insulin stimulated GLUT4 translocation (11), FSE mediated GLUT4 translocation involved only PKCλ. FSE regulates multiple targets involved in maintaining glucose homeostasis. It facilitates insulin secretion form pancreas, enhances liver GK activity. Both in muscles and liver cells, FSE induces phosphorylation of 1R, 1RS-1 and P13-K. This results in stimulation PKC and translocation of glucose transporters culminating in increases in glucose uptake (FIG. 12).

In conclusion, we have clearly shown in the present study that FSE, which has been used as a traditional medicine for diabetes, exhibited three types of antihyperglycemic effects: 1) it stimulated glucose dependent pancreatic insulin secretion, 2) metabolic effects in adipocytes and liver that enhanced uptake and, 3) enhanced glucose utilization by the activation of liver GK enzyme. Hence, the antidiabetic property of FSE is due to activation multiple pathways that control its glucose metabolism activity. This is a first report in which antidiabetic effect of any plant extracts has been thoroughly investigated and its mechanism of action unraveled. The study provides a starting point for revaluation usefulness of traditional medicinal plants for controlling hyperglycemia in diabetic condition.

EXAMPLES

Effect of FSE on diabetic mice. Hypoglycemic activity of plant extracts and other synthetic compound is conventionally assessed by inducing stable diabetes mellitus in a suitable animal and observing the changes in either fasting blood glucose (FBS) of by the intrapritoneal glucose tolerance test (IPGTT) in normal animal (29,30). The in vivo effectiveness of FSE was studied in diabetic fasted BALB/cJ or Swiss albino mice in which diabetes was induced by injecting multiple doses of STZ- or XN. The extract exhibited antihyperglycemic activity in a dose dependent manner, in both BALB/cJ and Swiss albino AXN-diabetic mice (FIGS. 1A and B). Injecting (I(P) 15 mg/kg FSE decreased blood glucose levels to normal by 4 h in both STZ and AXN induced diabetic mice. Overall 50-60% reduction was observed as compared to diabetic control ($P<0.01$). The peak effect occurred at 90 min after the administration of extract and the effects were comparable to that of 1.5 U/kg insulin. In STZ diabetic mice, blood glucose level decreased by 30%, in 90 min after the administration of FSE and it further lowered to half by 4 h (FIG. 1C). Blood glucose levels after 10 h of fasting in diabetic mice were measured on day 0, and 5, 10 and 15, after five consecutive intraperitoneal injections of 15 mg/kg FSE. As shown in FIG. 2A, the diabetic animal had significantly higher fasting blood glucose levels on day zero (239.5+/18.25 mg/dl). On day 5, the blood glucose concentration decreased significantly in diabetic mice treated with FSE and the mice became normoglycemic (136+/−29.5 mg/dl; $P<0.01$ vs. PBS-10 treated mice, 245+/−8.3 mg/dl). In extract treated mice, the antihyperglycemic effect of extract sustained up to tend days (160+/−14.5) without significant reduction in body weight (from 26.5+/−0.54 g on day zero to 25.5+/−0.41 g on day 10) as compared to diabetic animal group (from 27.0+/−0.4 g on day zero to 22.5+/−0-0.6 g on day 10; FIG. 2B). On day 15 the blood glucose level rose gradually to 184+/−20 mg/dl.

Effect of FSE on IPGTT in normal animals. The effect of FSE on IPGTT in normal Swiss albino mice was studied. We used 3 g/kg glucose to obtain a serum glucose level of ~25 mmol/l. As shown in FIG. 3A, 45 min after the administration of 15 mg/kg FSE, the rise in serum blood glucose level in experimental animal group (311.44+/−38.5) was significantly inhibited ($P<0.01$) as compared to the control group injected with PBS (549.44+/−11.69 mk/dl). Surprisingly, FSE had no effect on serum blood glucose level in glucose unloaded normoglycemic mice (FIG. 3B).

Effect of FSE on liver glucokinase activity. The GK activity in STZ-diabetic mice is extremely low due to partial or total deficiency of insulin resulting in derangement of carbohydrate metabolism. As insulin administration normalizes these alterations, activities of these enzymes represent a method to assess the effect of FSE on peripheral utilization of glucose. Since the extract showed a peak activity at 90 min after the administration, we explored the effect of FSE on GK activity at this time point. As expected STZ-diabetic BALB/cJ mice showed a significant reduction in the activity of GK by 47% in comparison with normal animal. Extract at a dose of 15 mg/kg enhanced the activity by 360% ($P<0.01$) as compared to diabetic control (Table). Further more, insulin treatment in diabetic mice improved GK activity by 460%.

Effect of FSE on insulin secretion in islets. Reduction in glucose level by 40-60% in diabetic mice by FSE raises the question as to whether or not the extract influences the insulin secretion for the observed antihperglycemic activity. To test this hypothesis, we studied the effect of FSE on isolated mouse islets of Lnagerhans. Islets were incubated in stimulating buffer (16.7 mM Glucose) for 60 min in the presence and absence of extract. When studied over a dose range, extract potentiated insulin secretion from islets in a gradual and dose dependent manner (FIG. 4). At a dose of 25 mg/l extract, insulin secretion increased by 48% ($P<0.05$).

Effect of FSE on glucose transport in GLUT4 overexpressing cells. Stable clone of CHO and 3T3-L1 cell lines that overexpress proteins involved in insulin signaling partway have been widely employed to study insulin induced glucose uptake and GLUT4 translocation (35-37). CHO cells overexpressing insulin receptor as well as GLUT4 were incubated in the presence of various concentrations of FSE for 30 min and glucose transport was measured by determining the rates 2DG uptake. FSE treatment exhibited a dose dependent increase in glucose transport rates of in this cell based model. The maximal effect was observed at 25 mg/l (270% of basal; $P<0.05$; FIG. 5A). However, the potency of FSE was ~35% less than insulin, in stimulating glucose uptake ($P<0.05$ vs. insulin; FIG. 5B) and FSE stimulated glucose uptake was abrogated by pretreating cells with wortmannin and BIS-1. To assess if the ability of FSE to enhance glucose transport involves GLUT4, its translocation was studied in GLUT4 overexpressing CHO- and 3T3-L1 cells by confocal microscopy, by ELISA and by membrane fractionation in 3T3-L1 adipocytes. FSE induced a significant increase in the GLUT4 fluorescence on the membrane of CHO-cells overexpressing insulin receptor as well as GLUT4 (FIG. 6), enhanced GLUT4 content in the membrane fraction of 3T3-L1 cells and, the translocation has increased by 50% in 3T3-L1 cells overexpressing GLUT4 $P<0.05$ vs. Basal). Pretreatment with wortmannin and BIS-1 masked these effects (FIGS. 7A and B).

Figure 8:
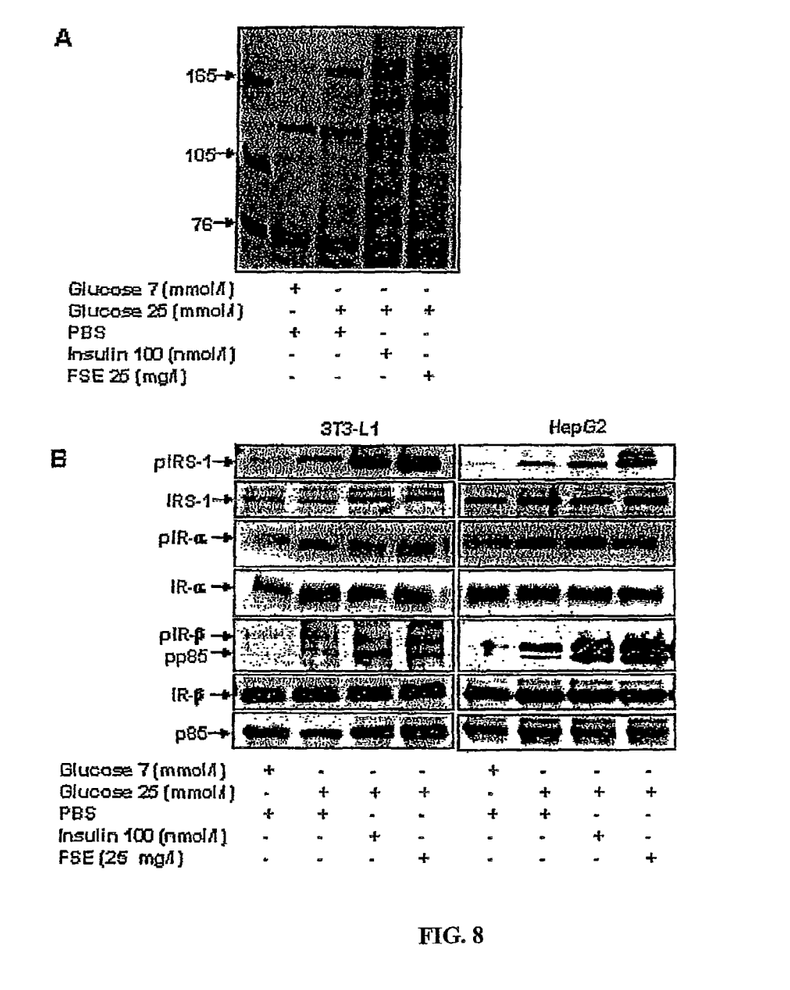
FIG. 8: Effect of FSE on cellular phosphorylation and insulin signaling proteins in 3T3-L1 adipocyte and HepG2 cells. Cellular phosphorylation pattern of both cell lines demonstrated that the effects of extract on cellular proteins are comparable to those induced by insulin.

Effect of FSE on cellular phosphorylation and insulin signaling proteins in 3T3-L1 adipocyte and HepG2 cells. The differentiated 3T3-L1 adipocytes, HepG2 cells, a human hepatoma cell line, are the classical model to elucidate the mechanism of action of antihyperglycemic compounds or plant extract. Activation of 1R by insulin results in increased phosphorylation of a number of proteins including, 1RS-1 and p85 subunit of P13-K. To explore the mechanism of action of action of FSE in differentiated 3T3-L1 adipocytes and HepG2 cells, they were treated with the 25 mg/l extract or 100 nmol/l insulin. Lysate from treated cells were subjected to western blot analysis using phosphoprotein specific antibodies. Cellular phosphorylation pattern of both cell lines demonstrated that the effects of extract of cellular proteins are comparable to those induced by insulin (FIG. 8). Similar to insulin treated cells, extract treated cells also did not exhibit 1R-$\alpha$ phosphorylation. Whereas the phosphorylation of 1R-$\beta$ and 1RS-1 and a major band at 85 kDa was comparable in both extract as well as insulin treated cells. Therefore it is reasonable to assume that the FSE induced phosphorylation pattern was similar in both HepG2 and 3T3-L1 cells.

The IR belongs to a family of receptor tyrosine kinase that shares high degrees of homology in the tyrosine kinase domain. Activation of receptor kinase leads to a wide variety of biological effects ranging from metabolic regulation to deleterious neoplastic transformation. To confirm the specificity of and to rule out that extract is a general receptor kinase activator, we tested the effect of extract on phosphorylation of EGF receptor in A431 cells. FSE failed to activate EGF receptor as treatment did not increase the autophosphorylation of it (FIG. 9). This data indicates that activation by the FSE is specific to 1R and its downstream signaling molecules in 3T3-L1 and HepG2 cells and hence, is not a general receptor tyrosine kinase activator.

Effect of FSE on PKCλ translocation in 3T3-L1 and RepG2 cells. Since Akt has been shown to be involved in insulin stimulated GLUT4 translocation we investigated the effect of PSE on Akt activation. Effect of insulin and extract on activation of Akt shows significant differences (FIG. 10). Extract did not induce Akt phosphorylation at Ser473 or Thr-308. To investigate the link between FSE induced 1R phosphorylation and GLUT4 translocation, translocation of PKCλ was studied in both 3T3-L1 and HepG2. Significant amount of PKCλ was detected in membrane fraction of FSE treated 3T3-L1 as compared to PBS treated (FIG. 11A). In unstimulated HepG2 cells the immunofluorescence was minimum as visualized by confocal microscopy. In contrast, stimulation of cells with FSE for 30 min resulted in maximum immunofluorescence on the cell surface and it was indistinguishable form that produced by treating cells with 100 nmol/l insulin for 10 min (FIG. 11B). This change in translocation are consistent with insulin dependent translocation of PKCλ from cytosol to cell surface. Wortmannin and bis-1 decreased the fluorescence associated with the membrane. This data indicates that extract acts through P13-K dependent pathway and thereby mediates PKCλ translocation.

TABLE 1

FSE enhances liver GK activity in STZ-BALB/cJ mice.

| | Non-diabetic control | Diabetic control | Insulin treated | FSE treated |
|---|---|---|---|---|
| GK activity $nmol \cdot min^{-1} \cdot mg^{-1}$ | 475.6 +/− 13.6 | 122.8 +/− 11.6 | 690.0 +/− 22.3* | 566.6 +/− 20.3* |

Liver was removed 90 min after the treatments and assayed for GK activity as described in RESEARCH DESIGN AND METHODS. (*P < 0.01 vs. diabetic control)

We claim:

1. A method of preparing a dialyzed aqueous extract of fenugreek seeds comprising:
    (a) washing fenugreek seeds in distilled water;
    (b) sterilizing the seeds to form sterilized seeds;
    (c) grinding the sterilized seeds to form a powder;
    (d) suspending the powder in phosphate buffered saline (PBS) comprising phenylmethylsulfonylflouride (PMSF) and a protease inhibitor cocktail to provide a suspension;
    (e) filtering the suspension to obtain a filtrate;
    (f) treating the filtrate with activated charcoal to obtain a clear supernatant;
    (g) subjecting the clear supernatant to a step of lyophilization to obtain a lyophilized powder
    (h) dissolving the lyophilized powder in phosphate buffered saline (PBS) to obtain a dissolved extract; and
    (i) dialyzing and storing the dissolved extract to obtain the dialyzed aqueous extract of fenugreek seeds.

2. The method of claim 1, wherein the step of sterilizing the seeds (b) is performed by soaking the seeds for 30 seconds in 0.1% sodium hypochlorite and 0.05% nonylphenoxypolyethoxyethanol.

3. The method of claim 2, wherein the sterilized seeds are rinsed thoroughly with distilled water after the sterilizing step.

4. The method of claim 1, wherein the PMSF the PBS is in an amount of 1 mmol/L.

5. The method of claim 4, wherein the pH of the PBS is 7.4.

6. The method of claim 1, wherein the sterilized seeds are ground under chilled conditions and wherein the chilled conditions result from applying liquid nitrogen to the sterilized seeds.

7. The method of claim 1, wherein the filtrate of step (f) is kept on ice for one hour after treatment with the activated charcoal and subsequently centrifuged at 15,000×g at 4° C. for 30 minutes to provide the clear supernatant.

8. The method of claim 1, wherein the dialyzing step (i) is dialyzed with an 8000 Dalton cut off dialysis membrane over a period of 24 hours after the powder is first dissolved in PBS and wherein during dialysis, a dialysis phosphate buffered saline (PBS) is changed every 6 hours.

9. The method of claim 1, wherein the dialyzed aqueous extract of fenugreek seed is stored at −70° C.

10. The method of claim 1, wherein the dialyzed aqueous extract of fenugreek seed has hypoglycemic activity.

11. The method of claim 10, wherein the hypoglycemic activity is mediated via stimulation of insulin signaling pathway, enhanced liver glucokinase activity and potentiation of glucose-dependent insulin secretion from islets.

12. The method of claim 1, wherein the dialyzed aqueous extract of fenugreek seeds stimulates glucose dependent pancreatic insulin secretion; creates metabolic effects in adipocytes and liver that enhances glucose uptake mediated via activation of insulation signaling pathway, and; and enhances glucose utilization by activation of liver GK enzyme.

* * * * *

UNITED STATES PATENT AND TRADEMARK OFFICE
CERTIFICATE OF CORRECTION

| | | |
|---|---|---|
| PATENT NO. | : 8,865,237 B2 | Page 1 of 1 |
| APPLICATION NO. | : 11/886267 | |
| DATED | : October 21, 2014 | |
| INVENTOR(S) | : Manoj Kumar Bhat et al. | |

It is certified that error appears in the above-identified patent and that said Letters Patent is hereby corrected as shown below:

TITLE PAGE: Item (73) Assignees, Line 3, delete "Pune (ID)" and insert -- Pune (IN) --

IN THE CLAIMS:

Column 12, Line 49, Claim 1, delete "pathway, and; and" and insert -- pathway; and --

Signed and Sealed this
Twenty-fourth Day of March, 2015

Michelle K. Lee
*Director of the United States Patent and Trademark Office*